United States Patent
Wu et al.

(10) Patent No.: US 9,448,217 B2
(45) Date of Patent: Sep. 20, 2016

(54) GAS SENSING SYSTEM

(71) Applicant: National Tsing Hua University, Hsinchu (TW)

(72) Inventors: Hsiang-Chiu Wu, Miaoli (TW); Shih-Wen Chiu, Taipei (TW); Ting-I Chou, Kaohsiung (TW); Chia-Min Yang, Hsinchu (TW); Da-Jeng Yao, Hsinchu (TW); Hsin Chen, HsinChu (TW); Kea-Tiong Tang, Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 386 days.

(21) Appl. No.: 14/194,882

(22) Filed: Mar. 3, 2014

(65) Prior Publication Data
US 2015/0136600 A1 May 21, 2015

(30) Foreign Application Priority Data
Nov. 18, 2013 (TW) .............................. 102141864 A

(51) Int. Cl.
*G01N 33/00* (2006.01)

(52) U.S. Cl.
CPC ...... *G01N 33/0032* (2013.01); *G01N 33/0022* (2013.01)

(58) Field of Classification Search
CPC ...................... G01N 33/0022; G01N 33/0032
See application file for complete search history.

(56) References Cited

U.S. PATENT DOCUMENTS

| 6,321,588 | B1 * | 11/2001 | Bowers | G01N 29/022 324/727 |
| 2002/0024662 | A1 * | 2/2002 | Ueno | G01N 21/0332 356/246 |

\* cited by examiner

*Primary Examiner* — Susan D Leong
(74) *Attorney, Agent, or Firm* — Birch, Stewart, Kolasch & Birch

(57) ABSTRACT

A gas sensing system includes an air intake hole which comprises a plurality of micro-flow channels, a replaceable sensor for receiving an air from the air intake hole and detecting the received air, and a processing unit coupled to the replaceable sensor and doing determination for the component of the air according to a detection result of the replaceable sensor. Wherein, the replaceable sensor includes a plurality of sensing chips arranged in an array and each sensing chip is coated with a sensing thin film separately to detect a different gas.

16 Claims, 3 Drawing Sheets

GAS SENSING SYSTEM

BACKGROUND OF THE INVENTION

1. Field of the Invention

The present invention relates to a gas sensing system, and more particularly to a replaceable gas sensing system which can be applied according to the different applications.

2. Description of Related Art

The gas sensing device can provide a standard for the gas to replace the uncertainty by human such that it is widely used in the energy, industry, agriculture, transportation, science, national defense, environmental protection and other fields. Although the gas sensing device has many applications, most of the gas sensing device is limited by the expensive prices and the inconvenience of carrying so that it cannot be applied popularly.

The design of the current gas sensing device is a customized design device in its algorithm and sensing chip for the gas waited to be detected. Therefore, the device and the algorithms can only detect specific gases, and they cannot widely detect a variety of gases at the same time.

Furthermore, in the actual environment, a gas will not exist alone, and it will mix with a variety of other gases. Therefore, the current gas sensing device has a high possibility of misjudgment, and its reliability is very low when the gas sensing device is detecting a gas.

SUMMARY OF THE INVENTION

The main object of the present invention is to provide a gas sensing system includes an air intake hole which comprises a plurality of micro-flow channels, a replaceable sensor for receiving an air from the air intake hole and detecting the received air, and a processing unit coupled to the replaceable sensor and doing determination for the component of the air according to a detection result of the replaceable sensor. Wherein, the replaceable sensor includes a plurality of sensing chips arranged in an array and each sensing chip is coated with a sensing thin film separately to detect a different gas.

DETAILED DESCRIPTION OF THE PREFERRED EMBODIMENT

The following content combines with the drawings and the embodiment for describing the present invention in detail.

Figure 1:
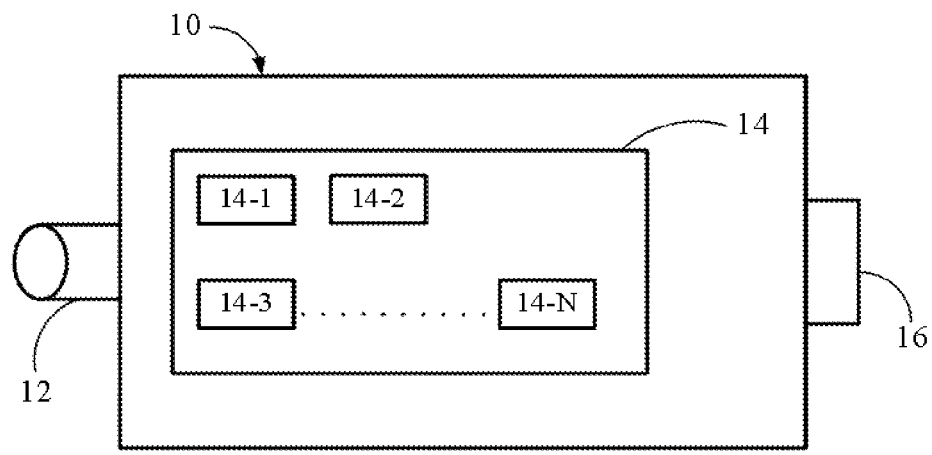
FIG. 1 is a schematic diagram of a gas sensing device which can combine with a mobile device according to an embodiment of the present invention.

As shown in FIG. 1, it is a schematic diagram of a gas sensing device 10 which can combine with a mobile device according to an embodiment of the present invention. The gas sensing device 10 includes an air intake hole 12, a sensor array 14, and a data output connector 16. In one embodiment, the sensor array 14 includes a plurality of sensor modules 14-1~14-N, wherein, a surface of each sensor module coats with a different sensing material according to the type of the gas to be detected. For example, a resistive sensing film composed of a polymer and a conductive carbon material. However, the present invention is not limited thereto. Each sensor module can be replaced respectively according to different applications.

Figure 2:
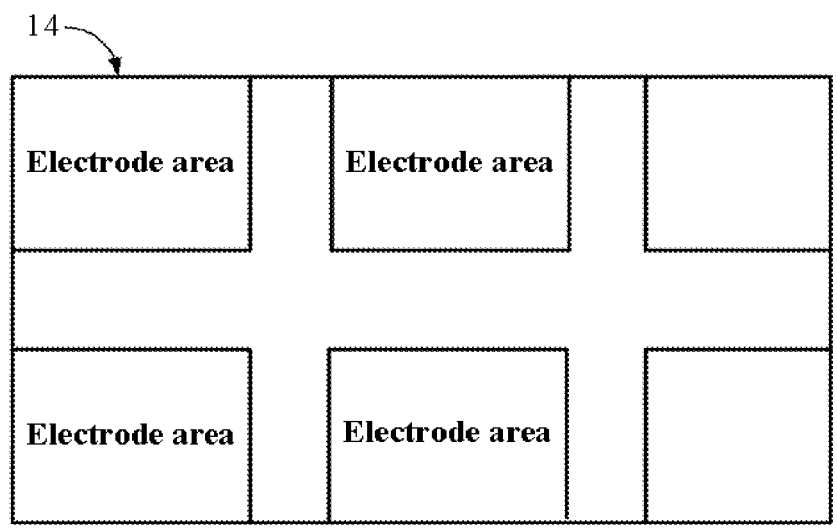
FIG. 2 is a schematic diagram of sensor array according to an embodiment of the present invention.

In one embodiment, the surfaces of the sensor modules 14-1~14-N covered with polymer material having a height (for example, a photoresist hiving a thickness of 50 um). As shown in FIG. 2, it is a schematic diagram of the sensor array 14 according to an embodiment of the present invention. From FIG. 2, the present invention coats with different materials at different electrode areas such that the sensor array 14 can distinguish different gases at the same time. The coating method may comprise inkjet, nano jet, screen printing, micro-contact printing, and pulsed laser vacuum deposition, etc. to form the sensor modules 14-1~14-N arranged in an array. Through the method of coating different materials at different electrode areas, the sensor array 14 capture data of a set of gases which comprises many gas combinations, not just data of single gas.

In one embodiment, the sensor array 14 is installed in the gas sensing device 10 by a type of solid-state memory card (e.g., Micro Secure Digital Card Micro SD) and achieves a replaceable function by combining with a corresponding socket.

In another embodiment, the air intake hole 12 of the gas sensing device 10 includes a plurality of micro-flow channels (not shown) to increase the sensitivity of the gas sensing device 10. The plurality of micro-flow channels are connected to a micro-cavity (not shown), wherein, the micro-cavity has a volume capacity and range such that the air can remain or mix. In one embodiment, the micro-cavity is a closed or open micro-cavity. In one embodiment, the closed micro-cavity has an exhaust device (not shown).

Figure 3:
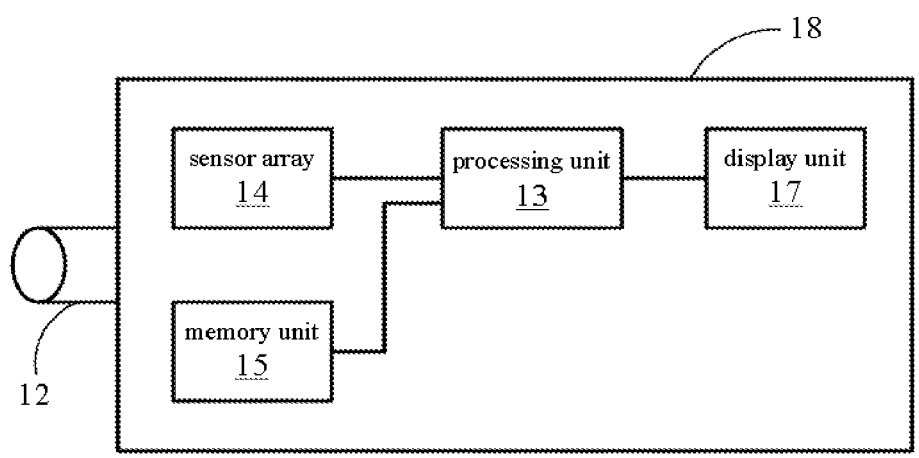
FIG. 3 is a schematic diagram of a gas sensing system having the gas sensing device shown in FIG. 1 according to an embodiment of the present invention.

FIG. 3 shows a schematic diagram of a gas sensing system 18 having the gas sensing device 10 shown in FIG. 1 according to an embodiment of the present invention. FIG. 3 will combine FIG. 1 for illustrating. As shown in FIG. 3, the gas sensing system 18 includes the gas sensing device 10, a processing unit 13, a memory unit 15, and a display unit 17. In one embodiment, the gas sensing system 18 utilizes the air intake hole 12 of the gas sensing device 10 to receive a gas, and utilizes the sensor array 14 to detect the data of the gas (e.g., the type or concentration of the gas etc.). Then, the gas sensing system 18 transmit the relative data of the gas to the processing unit 13. After the processing unit 13 receives the data of the gas, the processing unit 13 displays an analysis result to the display unit 17 for user to do determination through handing and comparing the data of the gas with the preset data stored in the memory unit 15 (for example, a database). In this embodiment, the gas sensing system 18 is a stand-alone operation type. Therefore, it can omit the data output connector of the gas sensing device 10.

Figure 4:
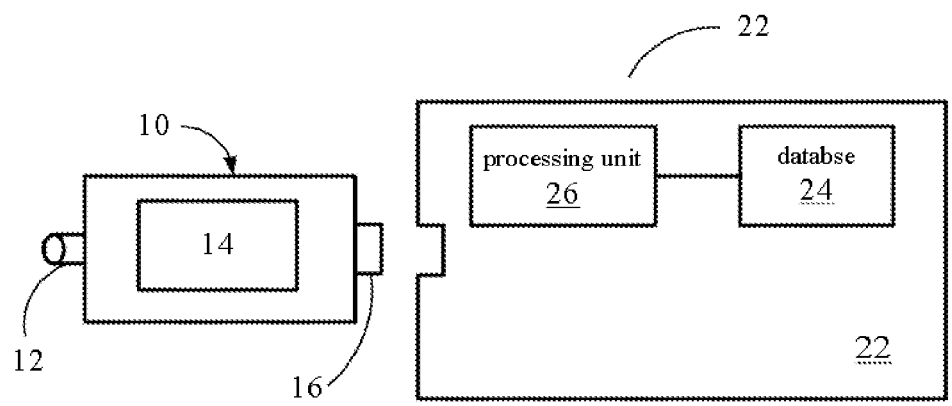
FIG. 4 is a schematic diagram of a gas sensing system having the gas sensing device shown in FIG. 1 according to another embodiment of the present invention.

FIG. 4 shows a schematic diagram of a gas sensing system 20 having the gas sensing device 10 shown in FIG. 1 according to another embodiment of the present invention. FIG. 4 will combine FIG. 1 for illustrating.

The gas sensing system 20 includes a gas sensing device 10 and a mobile device 22. In one embodiment, the gas sensing device 10 communicates with the mobile devices 22 (e.g., smart phone, tablet PC, or laptops, etc.) through a data output connector 16 (e.g., USB). The gas sensing device 10 transmits the gas data detected by it to the mobile device 22. It utilizes a processing unit 26 to cooperate with a database 24 for comparing, analyzing and processing the gas data.

Figure 5:
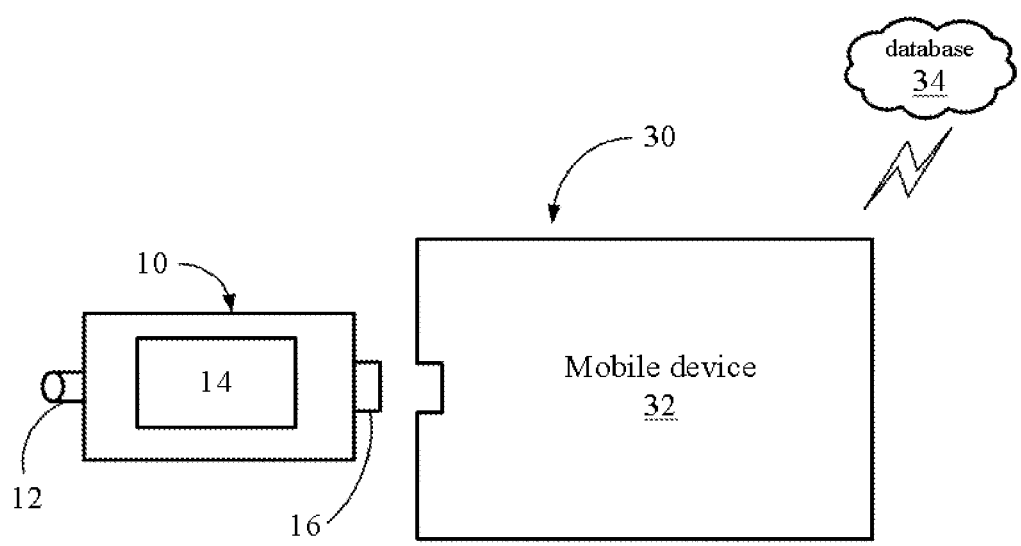
FIG. 5 is a schematic diagram of a gas sensing system having the gas sensing device shown in FIG. 1 according to another embodiment of the present invention.

FIG. 5 shows a schematic diagram of a gas sensing system 30 having the gas sensing device 10 shown in FIG. 1 according to another embodiment of the present invention. FIG. 5 will combine FIG. 1 for illustrating.

The gas sensing system 30 includes a gas sensing device 10, a mobile device 32, and a database 34. In one embodiment, the gas sensing device 10 communicates with the mobile device 32 (e.g., smart phone, tablet PC, or laptops, etc.) through the data output connector 16 (e.g., USB). The gas sensing device 10 transmits the gas data detected by it to the mobile device 32. In one embodiment, the mobile device 32 can utilize its communication function to download the data located at a cloud database 34 such that it compares, analyzes and processes the gas data inside the mobile device 32. Finally, the mobile device 32 utilizes its communication function (for example, Bluetooth or RF) to output the detected data.

In another embodiment, the mobile device 32 may also utilize its wireless transmission function to upload the gas data to the cloud database 34, and the gas data is compared, analyzed and processed in the cloud.

The present invention provides a replaceable gas sensing device and a system using the same. It utilizes the sensors to arrange in an array to forma gas sensing device capable of detecting a variety of gases at the same time, and then it utilizes a particular database and the algorithm to determine the received mixed gases.

Wherein, the sensor array of the sensing device is replaceable, and it can dispose different sensor arrays according to different applications. The reason why the sensor array can detect a variety of gases is that each sensor is coated with a different material. Therefore, each sensor can sense a different gas. The present invention can solve the traditional gas sensing device which can only detect one kind of gas, and also improve the drawback of the high error and low reliability.

The above embodiments of the present invention are not used to limit the claims of this invention. Any use of the content in the specification or in the drawings of the present invention which produces equivalent structures or equivalent processes, or directly or indirectly used in other related technical fields is still covered by the claims in the present invention.

What is claimed is:

1. A gas sensing system, comprising:
    an air intake hole including a plurality of micro-flow channels;
    a replaceable sensor receiving an air from the air intake hole, and detecting the air; and
    a processing unit coupled to the replaceable sensor and doing determination according to a detection result of the replaceable sensor;
    wherein, the replaceable sensor comprises a plurality of sensor chips arranged in an array, and each sensor chip is coated with a sensing thin film for detecting a different gas.

2. The gas sensing system according to claim 1, further comprising a data output connector for transmitting the detection result to the processing unit.

3. The gas sensing system according to claim 1, further comprising a memory unit coupled to the processing unit to provide a comparison base for the gas sensing system.

4. The gas sensing system according to claim 3, wherein the memory unit is disposed in a cloud.

5. The gas sensing system according to claim 4, further comprising a wireless module for downloading data located in the memory unit to the processing unit to do determination.

6. The gas sensing system according to claim 1, wherein the processing unit is disposed in a cloud.

7. The gas sensing system according to claim 6, further comprising a wireless module for uploading a determination result to the processing result to do determination.

8. The gas sensing system according to claim 1, wherein the sensing thin film utilizes an inkjet method to coat on a surface of each sensor chip.

9. The gas sensing system according to claim 1, wherein the sensing thin film utilizes a nano jet method to coat on a surface of each sensor chip.

10. The gas sensing system according to claim 1, wherein the sensing thin film utilizes a screen printing method to coat on a surface of each sensor chip.

11. The gas sensing system according to claim 1, wherein the sensing thin film utilizes a micro-contact printing method to coat on a surface of each sensor chip.

12. The gas sensing system according to claim 1, wherein the sensing thin film utilizes a pulsed laser vacuum deposition method to coat on a surface of each sensor chip.

13. The gas sensing system according to claim 1, further comprising a micro-cavity connected to the plurality of micro-flow channels, and the micro-cavity has a volume capacity and range such that the air can remain or mix.

14. The gas sensing system according to claim 13, wherein the micro-cavity is a closed type.

15. The gas sensing system according to claim 14, wherein the closed type micro-cavity has an exhaust device.

16. The gas sensing system according to claim 13, wherein the micro-cavity is an open type.

* * * * *